United States Patent

Corominas et al.

[11] Patent Number: 5,098,913
[45] Date of Patent: Mar. 24, 1992

[54] 7-(IMIDAZOL-1-YL)-1,4-DIHYDRO-4-OXO-6,8-DIFLUORO-1-CYCLOPROPYLQUINO-LONE-3-CARBOXYLIC ACID DERIVATIVES, THEIR PREPARATION AND THEIR APPLICATION AS DRUGS

[75] Inventors: Juan P. Corominas; Augusto C. Pinol; Jordi F. Constansa, all of Barcelona, Spain

[73] Assignee: Laboratorios Del Dr. Esteve, S.A., Barcelona, Spain

[21] Appl. No.: 653,856

[22] Filed: Feb. 8, 1991

Related U.S. Application Data

[63] Continuation of Ser. No. 330,190, Mar. 29, 1989, abandoned.

[30] Foreign Application Priority Data

Mar. 31, 1988 [FR] France .................. 88 04289

[51] Int. Cl.⁵ .................. C07D 401/10; A61K 31/47
[52] U.S. Cl. .................. 514/312; 546/156
[58] Field of Search .................. 546/156; 514/312

[56] References Cited

U.S. PATENT DOCUMENTS 4,530,930  7/1985  Uno et al. ............. 514/312
4,727,080  2/1988  Soler .................... 546/156

FOREIGN PATENT DOCUMENTS 3519286  12/1986  Fed. Rep. of Germany .

OTHER PUBLICATIONS

Petersen et al., Chemical Abstracts, vol. 106, No. 196270 (1987) (Abstract for DE 3519286, Dec. 4, 1986)

Primary Examiner—Mukund Shah
Assistant Examiner—E. Bernhardt
Attorney, Agent, or Firm—Dressler, Goldsmith, Shore, Sutker & Milnamow, Ltd.

[57] ABSTRACT

Novel heterocyclic compounds, characterized in that they have formula (I)

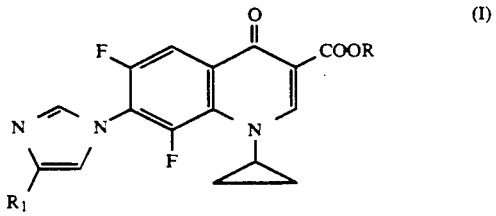

in which R represents a hydrogen atom, a lower alkyl radical or a phenyl or substituted phenyl radical and $R_1$ represents an alkyl radical or an aryl radical, and their physiologically acceptable salts.

4 Claims, No Drawings

7-(IMIDAZOL-1-YL)-1,4-DIHYDRO-4-OXO-6,8-DIFLUORO-1-CYCLOPROPYLQUINOLONE-3-CARBOXYLIC ACID DERIVATIVES, THEIR PREPARATION AND THEIR APPLICATION AS DRUGS

This application is a continuation of application Ser. No. 07/330,190, filed Mar. 29, 1989 now abandoned.

The present invention relates to novel derivatives of 1,4-dihydro-4-oxoquinoline-3-carboxylic acids substituted in the 7-position by a substituted 1-imidazole radical.

Imidazoles bonded to the 7-position of 1,4-dihydro-4-oxoquinoline-3-carboxylic acids have been studied very little. As far as it is known, there are only a small number of publications in the scientific literature which refer to this kind of compound.

German patent application A-3519286 describes 1-cyclopropyl-6,8-difluoro-1,4-dihydro-7-(imidazol-1-yl)-4-oxoquinoline-3-carboxylic acid.

In J. Med. Chem. 1984, 30, 2163, T. Uno et al. have described 1-ethyl-6-fluoro-7-(imidazol-1-yl)-4-oxoquinoline-3-carboxylic acid and its derivatives in which the imidazole carries substituents such as 2-methyl and 4-methyl, nitro, bromo, methylcarboxylate, dimethylcarboxamido, formyl, hydroxymethyl, dimethylaminomethyl and hydroxyiminomethyl.

The invention relates to compounds represented by formula (I) below

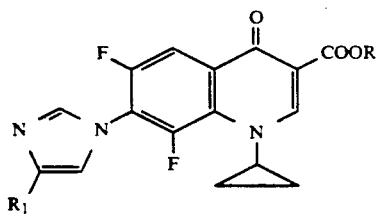

in which R represents a hydrogen atom, a lower alkyl radical or a phenyl or substituted phenyl radical and $R_1$ represents a lower alkyl radical or an aryl radical.

The present invention further relates to the physiologically acceptable salts of the compounds of general formula I.

The invention further relates to a pharmaceutical composition in which a compound of formula (I) or one of its pharmaceutically acceptable salts is present in an antimicrobially effective amount.

Furthermore, the invention relates to processes for the preparation of the compounds of formula (I) and their pharmaceutically acceptable salts.

Throughout the description, the term lower alkyl will denote linear or branched hydrocarbon radicals preferably containing from 1 to 4 carbon atoms.

The compounds of the invention which are represented by formula (I) can be prepared by a variety of known processes.

For example, one process consists in reacting a heterocyclic compound of formula (II)

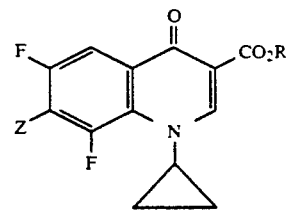

in which R is defined as above and Z represents a halogen atom, with an imidazole represented by formula (III)

in which $R_1$ is defined as above.

The reaction can be carried out in a large number of solvents. Examples which may be mentioned are lower alcohols such as ethanol, isopropanol, etc., ethers such as tetrahydrofuran, dioxane, diglyme, etc., nitriles such as acetonitrile, pyridine, dimethyl sulphoxide, dimethylformamide and hexamethylphosphorotriamide.

The above reaction can be carried out in the presence of an acid acceptor in an amount which is at least approximately between 1 and 2 mol per mol of compound of formula (II). Examples of appropriate acid acceptors which may be mentioned are alkali metal hydroxides, inorganic carbonates and tertiary amines such as triethylamine.

The compounds of formula (II) which can be used as starting materials to prepare the compounds of the invention represented by formula (I) are known compounds, such as those described for example in H. Koga, A. Itoh, S. Murayama, S. Suzue and T. Irikura, J. Med. Chem. 1980, 23, 1358.

The compounds of formula (III), which constitute other starting materials for preparing the compounds of the invention represented by formula (I), are also known or are synthesized as described for example in various articles: Bulavain et al., J. Chem. Soc. 1922, 947; Kunitake T. et al., Bull. Chem. Soc. Jpn. 1975, 48, 1304; Batterby et al., J. Chem. Soc. 1970, 49; Turner R. A. et al., J.A.C.S. 1949, 71, 2801; Hulball W. et al., J. Chem. Soc. 1928, 21; alternatively they are commercially available.

The above reaction can be carried out at atmospheric pressure or at a pressure of about 1 to 15 kg/cm$^2$, and at a temperature of about 10° to 50° C. for a period of about 1 to 5 days and then at a temperature of about 50° to 150° C. for a period of about 2 to 72 hours.

The preparation of novel derivatives according to the invention will be indicated in the following Examples. A few typical use forms will also be described for the different fields of application.

However, the Examples below, which are given simply by way of illustration, do not in any way limit the scope of the invention.

EXAMPLE 1

Preparation of 1-cyclopropyl-6,8-difluoro-7-(4-phenylimidazol-1-yl)-1,4-dihydro-4-oxoquinoline-3-carboxylic acid A mixture of 2.8 g (10 mmol) of 1-cyclopropyl-6,7,8-trifluoro-1,4-dihydro-4-oxoquinoline-3-carboxylic acid, 4.3 g (30 mmol) of 4-phenylimidazole, 20 ml of triethylamine and 100 ml of DMSO is refluxed for 3 hours. It is allowed to cool, poured into a water/ice mixture and adjusted to pH 5 to give a precipitate, which is filtered off and washed with water. The solid is dried under vacuum to give 2.3 g of 1-cyclopropyl-6,8-difluoro-7-(4-phenylimidazol-1-yl)-1,4-dihydro-4-oxoquinoline-3-carboxylic acid melting at 286°–288° C.

Spectroscopic data: $^1$H NMR [DMSO-d$_6$], δ:1.29 (b, 4H); 4.10 (m, 1H); 7.33 (m, 3H); 7.90 (m, 5H); 8.80 (s, 1H).

IR (KBr): 3115, 3050, 1735, 1470 cm$^{-1}$.

EXAMPLE 2

Preparation of 1-cyclopropyl-6,8-difluoro-7-(4-methylimidazol-1-yl)-1,4-dihydro-4-oxoquinoline-3-carboxylic acid A mixture of 2.8 g (10 mmol) of 1-cyclopropyl-6,7,8-trifluoro-1,4-dihydro-4-oxoquinoline-3-carboxylic acid, 2.1 g (25 mmol) of 4-methylimidazole, 30 ml of triethylamine and 150 ml of acetonitrile is refluxed for 5 hours. It is concentrated under reduced pressure and the precipitate is filtered off. The residue is taken up in 50 ml of water, the pH is adjusted to 5 and the precipitate is filtered off and washed. It can be recrystallized from acetonitrile.

This gives 2.3 g of 1-cyclopropyl-6,8-difluoro-7-(4-methylimidazol-1-yl)-1,4-dihydro-4-oxoquinoline-3-carboxylic acid melting at 215°–223° C.

Spectroscopic data: $^1$H NMR [DMSO-d$_6$], δ:1.29 (b, 4H); 2.23 (s, 3H); 3.27 (b, H$_2$O); 4.15 (m, 1H); 7.16 (s, 1H); 7.85 (s, 1H); 8.10 (d, 1H); 8.8 (s, 1H).

IR (KBr): 3050, 1735, 1615 cm$^{-1}$.

Antimicrobial Pharmacological Activity (G. L. Daquet and Y. A. Chabbect, Techniques en bactériologie (Techniques in bacteriology), vol. 3, Flammarion Médecine-Sciences, Paris, 1972, and W. B. Hugo and A. D. Rusell, Pharmaceutical Microbiology, Blackwell Scientific Publications, London, (1977))

Culture Medium and Solvent

No. 1 agar for antibiotics (Oxoid OM 327)
Tryptone-soya broth (Oxoid OM 129)
Ringer ¼ physiological solution (Oxoid BR 52)
Dextrose agar (BBL-11165)
0.1N NaOH

Microorganisms

"*Bacillus subtilis*" ATCC 6633
"*Citrobacter freundii*" ATCC 11606
"*Enterobacter aerogenes*" ATCC 15038
"*Enterobacter cloacae*" ATCC 23355
"*Escherichia coli*" ATCC 10536
"*Escherichia coli*" ATCC 23559
"*Klebsiella pneumoniae*" ATCC 10031
"*Proteus mirabilis*" ATCC 4675
"*Proteus vulgaris*" ATCC 8427
"*Pseudomonas aeruginosa*" ATCC 9721
"*Pseudomonas aeruginosa*" ATCC 10145
"*Salmonella typhimurium*" ATCC 14028
"*Serratia marcescens*" ATCC 13880
"*Shigella flexneri*" ATCC 12022
"*Staphylococcus aureus*" ATCC 25178
"*Streptococcus faecalis*" ATCC 10541

Preparation of the Inoculations

Each of the microorganisms is inoculated by streak plating in tubes of no. 1 agar for antibiotics and incubated for 20 hours at 37° C. A culture loop is then taken, inoculated in a tryptone-soya broth and incubated for 20 hours at 37° C. The culture obtained is diluted to ¼ with a Ringer physiological solution so as to give a normalized suspension of $10^7$–$10^9$ cfu/ml for each organism.

Preparation of the Medium Containing the Derivatives of General Formula I

Starting from a solution of 1000 µg/ml in 0.1N NaOH, each product is diluted in dextrose agar (previously melted and kept at 50° C.) by means of successive dilutions so as to give the following concentrations: 64-32-16-8-4-2-1-0.5-0.25-0.125-0.06-0.03 µg of derivative/ml of the medium.

Each concentration of each product is subsequently divided up into Petri dishes of diameter 10 cm, at a rate of 10 ml of medium per dish, there being as many dishes as microorganisms to be tested.

When the medium has cooled, the dishes are inoculated with the inoculations at a rate of 0.4 ml of inoculation per dish. They are spread with a Drigalski loop and the supernatant is collected. The inoculated dishes are incubated at 37° C. for 20 hours.

Results

The results obtained are described in Table I. The compounds of the Examples have a greater "in vitro" activity than pipemidic acid, as regards both Enterobacteriaceae (*Pseudomonas aeruginosa*) and Gram-positive cocci. The compounds of the Examples have a greater activity than pipemidic acid against Gram-positive cocci and against Gram-negative microorganisms.

TABLE I

CMI "in vitro" compared with pipemidic acid
The concentrations are given in µg/ml.

|  | Compound of Example 2 | Pipemidic acid | Compound of Example 1 |
| --- | --- | --- | --- |
| *Bacillus subtilis* ATCC 6633 | ≦0.03 | 8 | ≦0.03 |
| *Citrobacter freundii* ATCC 11606 | 0.12 | 4 | 2 |
| *Enterobacter aerogenes* ATCC 15038 | 0.25 | 32 | 2 |
| *Enterobacter chloacae* ATCC 23335 | 0.12 | 8 | 2 |
| *Escherichia coli* ATCC 10536 | 0.25 | 2 | 2 |
| *Escherichia coli* ATCC 23559 | 0.12 | 16 | 1.0 |
| *Klebsiella pneumoniae* ATCC 10031 | ≦0.03 | 2 | 0.25 |
| *Proteus mirabilis* ATCC 4675 | 0.50 | 16 | 4 |
| *Proteus vulgaris* ATCC 8427 | 0.12 | 8 | 1 |
| *Pseudomonas aeruginosa* ATCC 9721 | 2.0 | 32 | 4.0 |

TABLE I-continued

| | Compound of Example 2 | Pipemidic acid | Compound of Example 1 |
|---|---|---|---|
| CMI "in vitro" compared with pipemidic acid. The concentrations are given in μg/ml. | | | |
| *Pseudomonas aeruginosa* ATCC 10145 | 4.0 | 32 | 16 |
| *Salmonella typhimurium* ATCC 14028 | 0.25 | 4 | 2 |
| *Serratia marcescens* ATCC 13880 | 0.50 | 16 | 4 |
| *Shigella flexnerii* ATCC 12022 | 0.25 | 4 | 0.5 |
| *Staphylococcus aureus* ATCC 25178 | 0.06 | 64 | 0.06 |
| *Streptococcus faecalis* ATCC 10541 | 0.25 | 64 | 0.12 |

In view of their good pharmacological properties, the derivatives of general formula I are therefore capable of being used in human and/or veterinary medicine for the treatment of systemic or localized acute, chronic and recurrent infections caused by Gram-positive and Gram-negative microorganisms sensitive to the products forming the subject of the present invention, in the gastro-intestinal or urogenital tract, the respiratory apparatus, the skin and the soft tissues, as well as neurological and odontostomatological infections.

In human therapy, the proposed dose of the derivatives of the present invention is between about 400 and 1200 mg/day for an adult, administered for example in the form of tablets or gelatin capsules. However, this dosage can vary according to the severity of the complaint.

Two particular pharmaceutical forms of the derivatives forming the subject of the present invention will be indicated below as Examples.

| Example of tablet formulation | |
|---|---|
| Compound of Example 2 | 0.400 g |
| Carboxymethyl starch | 0.018 g |
| Polyvinylpyrrolidone K29-32 | 0.030 g |
| Microcrystalline cellulose | 0.146 g |
| Colloidal silica | 0.003 g |
| Magnesium stearate | 0.003 g |
| | 0.600 g |
| Example of gelatin capsule formulation | |
| Compound of Example 2 | 0.400 g |
| Microcrystalline cellulose | 0.0356 g |
| Colloidal silica | 0.0022 g |
| Magnesium stearate | 0.0022 g |
| | 0.440 g |

We claim:
1. A compound of the formula:

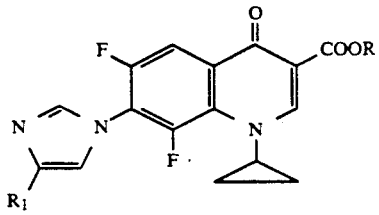

in which
R is hydrogen and
$R_1$ is selected from the group consisting of lower alkyl radicals and the phenyl radical, and their physiologically acceptable salts.

2. A compound selected from the group consisting of 1-cyclopropyl-6,8-difluoro-7-(4-phenyl-imidazol-1-yl)-1,4-dihydro-4-oxoquinoline-3-carboxylic acid and 1-cyclopropyl-6,8-difluoro-7-(4-methylimidazol-1-yl)-1,4-dihydro-4-oxoquinoline-3-carboxylic acid.

3. A method of treating bacterial infections comprising the step of administering a therapeutically effective amount of a compound of claim 2.

4. An antibacterial pharmaceutical composition comprising a pharmaceutically acceptable carrier and an antibacterially effective amount of a compound of claim 2.

* * * * *